(12) United States Patent
Macke et al.

(10) Patent No.: US 7,122,622 B2
(45) Date of Patent: Oct. 17, 2006

(54) PEPTIDE COMPOUNDS HAVING IMPROVED BINDING AFFINITY TO SOMATOSTATIN RECEPTORS

(75) Inventors: Helmut Robert Macke, Loerrach (DE); Jean-Claude Reubi, Wabern (CH); Jörg Simon Schmitt, Thal (CH); Mihaela Ginj, Basel (CH)

(73) Assignee: BioSynthema Inc., Saint Louis, MO (US)

( * ) Notice: Subject to any disclaimer, the term of this patent is extended or adjusted under 35 U.S.C. 154(b) by 254 days.

(21) Appl. No.: 10/417,072

(22) Filed: Apr. 16, 2003

(65) Prior Publication Data

US 2004/0044177 A1     Mar. 4, 2004

Related U.S. Application Data

(60) Provisional application No. 60/319,189, filed on Apr. 16, 2002.

(51) Int. Cl.
| | | |
|---|---|---|
| A61K 38/31 | (2006.01) | |
| C07K 16/00 | (2006.01) | |
| C07K 17/00 | (2006.01) | |
| C07K 5/00 | (2006.01) | |
| C07K 7/00 | (2006.01) | |

(52) U.S. Cl. .................................... 530/311
(58) Field of Classification Search ............... 530/311
See application file for complete search history.

(56) References Cited

U.S. PATENT DOCUMENTS

| | | | | |
|---|---|---|---|---|
| 4,853,371 | A * | 8/1989 | Coy et al. ............... | 514/12 |
| 4,904,642 | A * | 2/1990 | Coy et al. ............... | 514/11 |
| 5,750,499 | A | 5/1998 | Hoeger et al. | |
| 5,821,221 | A * | 10/1998 | Shalaby et al. ......... | 514/9 |
| 5,968,903 | A * | 10/1999 | Kaneko et al. ......... | 514/9 |
| 5,980,945 | A * | 11/1999 | Ruiz ....................... | 424/484 |
| 6,204,256 | B1 * | 3/2001 | Shalaby et al. ......... | 514/58 |
| 6,262,229 | B1 * | 7/2001 | Coy et al. ............... | 530/311 |
| 2003/0114362 | A1 * | 6/2003 | Gruner et al. ........... | 514/8 |
| 2004/0102364 | A1 * | 5/2004 | Bonasera et al. ........ | 514/9 |

FOREIGN PATENT DOCUMENTS

| | | |
|---|---|---|
| WO | WO 97/01579 A | 1/1997 |
| WO | WO 98/41540 A | 9/1998 |
| WO | WO 01/81426 A | 11/2001 |
| WO | WO 02/100885 A | 12/2002 |

OTHER PUBLICATIONS

M. Ginj et al., "Dota-Noc, A High Affinity Ligand for Somatostatin Receptor Subtypes 2, 3 and 5"; Fifth International Electronic Conference on Synthetic Organic Chemistry, Sep. 2001, Internet.

M. Ginj et al., "Dota-Noc, A High Affinity Ligand for Somatostatin Receptor Subtypes 2, 3 and 5"; European Journal of Nuclear Medicine, vol. 28, No. 8, 2001, p. 966.

Rossowski, et al., "Potent Inhibitory Effects of a Type Four Receptor-Selective Somatostatin Analog on Rat Insulin Release", Biochemical and Biophysical Research Communications, vol. 197, No. 2, Dec. 15, 1993, pp. 366-371, Academic Press, U.S.A.

Reubi, et al., "Affinity Profiles for Human Somatostatin Receptor Subtypes SST1-SST5 of Somatostatin Radiotracers Selected for Scintigraphic and Radiotherapeutic Use", European Journal of Nuclear Medicine, vol. 27, No. 3, Mar. 2000, pp. 273-282, Springer-Verlag Heidelberg, Germany.

Fagan, et al., "Insulin Secretion in Inhibited by Subtype Five Somatostatin Receptor in the Mouse", Surgery, vol. 124, No. 2, Aug. 1998, pp. 254-259, Mosby, Inc., St. Louis, MO.

M. Ginj et al., "Synthesis and Biological Activity of a New and Highly Potent Ligand for Somatostatin Receptors 2, 3 and 5.", Journal of Peptide Science, vol. 8, No. Supplement, Aug. 2002, pp. S68, John Wiley & Sons, Ltd.

Schmitt et al., "Dota-Noc, a High Affinity Ligand of the Somatostatin Receptor Subtypes Subtypes 2, 3 and 5 for Radiotherapy", Journal of Labelled Compounds and Radiopharmaceuticals, vol. 44, Supplement 1, May 2001, pp. S697-S699, Switzerland.

Bruns, et al., "Binding Properties of Somatostatin Receptor Subtypes." Metabolism Clinical and Experimental, vol. 45, No. 8, Suppl. 1, 1996, pp. 17-20.

Lewis, et al., "Synthesis of Somatostatin Analogs Incorporating Nucleo Amino Acids", Tetrahedron, vol. 50, No. 25, 1994, pp. 7485-7494, Elsevier Science Ltd., Great Britain.

Pinski, et al., "Somatostatin Analog RC-160 and Bombesin/Gastrin-Releasing Peptide Antagonists RC-3095 Inhibit the Growth of Androgen-Independent DU-145 Human Prostate Cancer Line in Nude Mice", Cancer Letters, vol. 71, No. 1-3, 1993, pp. 189-196, Elsevier Scientific Publishers Ireland Ltd., Ireland.

* cited by examiner

Primary Examiner—Bruce R. Campell
Assistant Examiner—Marcela M Cordero Garcia
(74) Attorney, Agent, or Firm—Thompson Coburn LLP

(57) ABSTRACT

The invention relates to a peptide compound having an improved binding affinity to somatostatin receptors, comprising a somatostatin analogue as the peptide and a chelating group covalently linked to the N-terminal free amino group of said peptide, wherein said somatostatin analogue carries an 1-naphthylalanine or a 3-benzothienylalanine residue in its 3-position. The invention further relates to said peptide compound labeled with a detectable element or with a therapeutic radionuclide, as well as to a diagnostic method and to a method for the therapeutic treatment of tumors, by using the labeled compounds.

20 Claims, 1 Drawing Sheet

PEPTIDE COMPOUNDS HAVING IMPROVED BINDING AFFINITY TO SOMATOSTATIN RECEPTORS

APPLICATION CROSS REFERENCE

This application claims the priority benefit of Provisional Application Ser. No. 60/319,189 filed Apr. 16, 2002 the teachings of which are hereby incorporated by reference.

BACKGROUND OF INVENTION

The invention relates to a peptide compound having an improved binding affinity to somatostatin receptors, comprising a somatostatin analogue as the peptide and a chelating group covalently linked to the N-terminal free amino group of said peptide Such peptide compounds and their radiolabelled derivatives can be used for therapy of somatostatin—receptor positive tumors. Detectably labeled somatostatin—peptide compounds are also useful for in vivo imaging. See in this respect the patent publications of Albert et al. (U.S. Pat. No. 5,753,627; U.S. Pat. No. 5,776,894), of Krenning et al. (U.S. Pat. No. 6,123,916), of De Jong et al. (WO 00/18440), and of Srinivasan et al. (U.S. Pat. Nos. 5,804,157; 5,830,431). Albert et al., disclose complexed somatostatin peptides for in vivo imaging of somatostatin receptor—positive tumors, which peptides are derived from somatostatin analogues, carrying an optionally substituted phenylalanine residue or a beta- or 2-naphthylalanine residue in its 3-position. Selective internal tumor therapy with radiolabelled peptides has become very important in nuclear medicine in the past years. Especially somatostatin derivatives have been successfully applied in the clinic for tumor diagnosis and therapy, showing that the principle of receptor targeting is working in practice. For more than four years already much experience has been gained in clinical trials with the use of $^{90}$Y—labeled DOTA-[Tyr$^3$]-octreotide (DOTA-TOC) for tumor therapy (M. de Jong: Eur. J. Nucl. Med. 26, 1999, 693–698). Yet DOTA-TOC only shows high affinity to the somatostatin receptor subtype 2 (sst 2), whereas the affinity to other somatostatin subtypes, in particular sst 3 and sst 5, which are found also in a variety of tumors, is too low to contribute essentially to tumor targeting. For example, most thyroid tumors express these last-mentioned somatostatin receptor subtypes, but have only low levels of sst 2 (E. B. Forssell-Aronsson et al.: J. Nucl. Med. 41, 2000, 636–642).

SUMMARY OF THE INVENTION

It is the objective of the present invention to provide a peptide compound which has a considerable binding affinity to a plurality of somatostatin receptor subtypes, compared with the above known somatostatin peptides. It is an additional advantage if such a peptide compound should have a substantially improved overall affinity to somatostatin receptors. On account of its multispecificity, such a peptide compound, in particular after labeling with a suitable radionuclide, could be therapeutically used for treating a broader variety of tumors. In addition, after labeling with a suitable detectable element, such a peptide compound should have an improved suitability for in vivo detecting and localizing tissues, in particular tumors and metastases thereof, carrying somatostatin receptor types in varying levels.

This objective can be achieved, according to the present invention, by a peptide compound as defined herein, wherein said somatostatin analogue carries an 1-naphthylalanine or a 3-benzothienylalanine residue in its 3-position.

It has been found, that the new peptide compounds of the invention have an unexpectedly high affinity to a plurality of somatostatin receptor subtypes. This favorable binding affinity makes the new peptide compounds promising candidates both for diagnosis, after labeling, and for tumor therapy. Internalization experiments show a substantially increased internalization rate. Biodistribution experiments in vivo show that the labeled new peptide compounds of the invention have a significantly higher tumor uptake than known somatostatin peptide derivatives.

More in particular, the present invention relates to a new peptide compound as defined above, wherein the peptide is a somatostatin analogue of the general formula

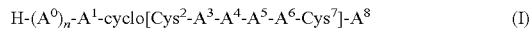

wherein:
n is 0 or 1,
A$^0$ is optionally halogenated Tyr or Phe,
A$^1$ is optionally halogenated Tyr, or optionally halogenated or methylated Phe or Nal,
A$^3$ is 1-Nal or 3-benzothienylalanyl,
A$^4$ is Trp, optionally N-methylated in its side-chain,
A$^5$ is Lys, optionally N-methylated in its side-chain,
A$^6$ is Thr, Val, Ser, Phe or Ile, and
A$^8$ is Thr, Trp or Nal, wherein the terminal carboxy group may be modified to an alcohol or an, optionally C1–C3 alkylated, amide group.

Suitable examples of the above new somatostatin analogues of formula I are:

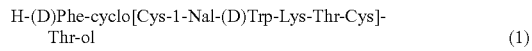

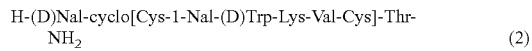

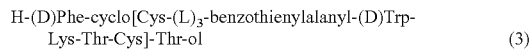

The above examples are covered by the general formula II, encompassing preferred somatostatin analogues:

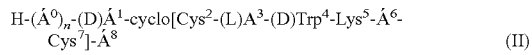

wherein:
n is 0 or 1,
Á$^0$ is optionally halogenated Tyr,
Á$^1$ is optionally halogenated Tyr, or Phe, or Nal,
A$^3$ is 1-Nal or 3-benzothienylalanyl,
Á$^6$ is Thr or Val, and
Á$^8$ is Thr-ol, Thr-OH or Thr-NH$_2$.

The inventors have already disclosed results of the above labeled compound (1) of their invention at two Symposia, viz. at Jun. 11–15, 2001, and at Aug. 26–29, 2001. These presentations have been published as Symposium Abstracts in J. Labeled Cpd. Radiopharm. 44, Suppl. 1 (2001), 5697–5699, and in Eur. J. Nucl. Med. 28/8, OS 24 (2001), 966, respectively.

The peptide compound according to the invention comprises a chelating group covalently linked to the N-terminal free amino group of the peptide. Various well-known chelating groups can be used, for example, those selected from:

(i) N$_2$S$_2$-, N$_3$S- and N$_4$-tetradentate ring structure containing groups, (ii) isocyanate, carbonyl, formyl, diazonium, isothiocyanate and alkoxycarbimidoyl containing groups, (iii) groups derived from N-containing di- and polyacetic acids and their derivatives, and from (iv) 2-iminothiolane and 2-iminothiacyclohexane containing groups. The chelating groups sub (iii) above are preferred, encompassing chelating groups derived from ethylenediamine tetraacetic acid (EDTA), diethylenetriamine pentaacetic acid (DTPA), ethyleneglycol-OO'-bis(2-aminoethyl)-N,N,N',N'-tetraacetic acid (EGTA), N,N'-bis(hydroxybenzyl)ethylenediamine-N,N'-diacetic acid (HBED), triethylenetetramine hexaacetic acid (TTHA), substituted EDTA or DTPA, 1,4,7,10-tetraazacyclododecane-N,N', N'',N'''-tetraacetic acid (DOTA), 1,4,7-triazacyclonane-1,4,7-triacetic acid (NOTA) or 1,4,8,11-tetraazacyclotetradecane-N,N',N'',N'''-tetraacetic acid (TETA).

The method of linking the chelating group to the somatostatin analogue for obtaining the peptide compound of the invention is generally known in the art. The synthesis of the peptide compound having the above chelating group sub (iv) is described in WO 89/07456.

Generally, for the purpose in view, the peptide compound of the invention is labeled with a detectable element selected from gamma- or positron-emitting radionuclides, Auger-electron-emitting isotopes and paramagnetic ions of nonradioactive elements, or with a therapeutic radionuclide. Suitable detectable elements for imaging purposes are gamma- or positron-emitting radionuclides, selected from the group consisting of $^{99m}$Tc, $^{203}$Pb, $^{66}$Ga, $^{67}$Ga, $^{68}$Ga, $^{72}$As, $^{111}$In, $^{113m}$In, $^{97}$Ru, $^{62}$Cu, $^{64}$Cu, $^{52}$Fe, $^{51}$Cr, $^{24}$Na, $^{157}$Gd, $^{52m}$Mn, $^{162}$Dy, $^{123}$I, $^{131}$I, $^{75}$Br and $^{76}$Br, or paramagnetic ions of elements, selected from the group consisting of nonradioactive Gd, Fe, Mn and Cr. In addition to the use of radioisotopes as detectable elements, which enables in vivo detection by a gamma camera, paramagnetic ions of nonradioactive elements, such as Gd, Fe, Mn or Cr, preferably of Gd, can be used, viz. for in vivo detection by MRI.

For therapeutic purposes the compounds of the invention can advantageously be labeled with therapeutic radionuclides, selected from the group consisting of $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{109}$Pd, $^{165}$Dy, $^{177}$Lu, $^{161}$Tb, $^{211}$At, $^{123m}$Rh, $^{111}$In and $^{153}$Sm.

Chelation of the above metal isotopes can easily be effected in a manner known per se for related compounds, for example, by bringing the peptide compound of the invention in contact with a compound, often a salt, of the desired isotope in a suitable solvent or diluent, if desired at higher temperature. The preparation of radioactive-halogen labeled peptide compounds according to the present invention can be carried out by a method as described for related compounds in the above-mentioned WO 00/18440, in order to introduce the desired halogen radionuclide into an aromatic nucleus in position 0 or 1 of the peptide. This labeling can conveniently be performed by introducing a halogen atom or a radioactive halogen atom into an radioactive nucleus, preferably an activated aromatic nucleus such as tyrosyl, present in the above position in the peptide compound, if necessary followed by exchange with the desired halogen radionuclide. The radiohalogenation reaction is preferably performed by reacting the peptide compound with a solution of an alkali metal radionuclide selected from $^{123}$I⁻, $^{131}$I⁻, $^{211}$At⁻, $^{75}$Br⁻ and $^{76}$Br⁻ under the influence of a halide-oxidizing agent, such as chloramine T or iodogen. Alternatively, the above substitution reaction can be carried out with nonradioactive halogen, after which halo-exchange with radioactive halogen is performed, e.g. as described in European patent 165630.

The present invention further relates to a pharmaceutical composition, comprising in addition to a pharmaceutically acceptable carrier and, if desired, at least one pharmaceutically acceptable adjuvant, as the active substance a labeled peptide compound as defined above, or a pharmaceutically acceptable salt thereof. Such pharmaceutical compositions can be used for diagnostic purposes; then the peptide compounds are provided with detectable elements as described above. If the compositions are intended for tumor therapy, advantageously the above-mentioned therapeutic radionuclides can be used for labeling the peptide compounds.

The present invention also relates to a method for detecting and localizing tissues having somatostatin receptors in the body of a warm-blooded living being, This diagnostic method comprises (i) administering to said being a pharmaceutical composition, labeled with a suitable detectable element, as defined above, comprising the active substance in a quantity sufficient for external imaging, and thereupon (ii) subjecting said being to external imaging to determine the targeted sites in the body of said being in relation to the background activity, in order to allow detection and localization of said tissues in said body. The present invention further relates to a method for the therapeutic treatment of tumors, having on their surface somatostatin receptors, in the body of a warm-blooded living being, which comprises administering to said being a pharmaceutical composition labeled with a suitable therapeutic radionuclide, as defined above, comprising the active substance in a quantity effective for combating or controlling tumors.

It is sometimes hardly possible to put the ready-for use radiolabelled composition at the disposal of the user, in connection with the often poor shelf life of the radiolabelled peptide compound and/or the short half-life of the radionuclide used. In such cases the user can carry out the labeling reaction with the radionuclide in the clinical hospital or laboratory. For this purpose the various reaction ingredients are then offered to the user in the form of a so-called "kit". It will be obvious that the manipulations necessary to perform the desired reaction should be as simple as possible to enable the user to prepare from the kit the radioactive-labeled composition by using the facilities that are at his disposal. Therefore the invention also relates to a kit for preparing a radiopharmaceutical composition. Such a kit according to the present invention may conveniently comprise a peptide compound as defined hereinbefore, viz. derived from a somatostatin analogue carrying an 1-naphthylalanine or 3-benzothienylalanine residue in its 3-position, to which substance, if desired, an inert pharmaceutically acceptable carrier and/or formulating agents and/or adjuvants are added, (ii) a solution of a radionuclide compound selected from the group consisting of $^{99m}$Tc, $^{203}$Pb, $^{66}$Ga, $^{67}$Ga, $^{68}$Ga, $^{72}$As, $^{211}$At, $^{111}$In, $^{113m}$In, $^{97}$Ru, $^{62}$Cu, $^{64}$Cu, $^{52}$Fe, $^{52m}$Mn, $^{51}$Cr, $^{24}$Na, $^{157}$Gd, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{109}$Pd, $^{165}$Dy, $^{177}$Lu, $^{161}$Tb, $^{123m}$Rh and $^{153}$Sm, and (iii) instructions for use with a prescription for reacting the ingredients present in the kit. The kit according to the invention preferably comprises a peptide compound derived from a somatostatin analogue of the general formula I, wherein the symbols have the meanings given hereinbefore.

BRIEF DESCRIPTION OF DRAWINGS

For a better understanding of the present invention, reference may be made to the accompanying drawing win which.

DETAILED DESCRIPTION OF THE INVENTION

Figure 1:
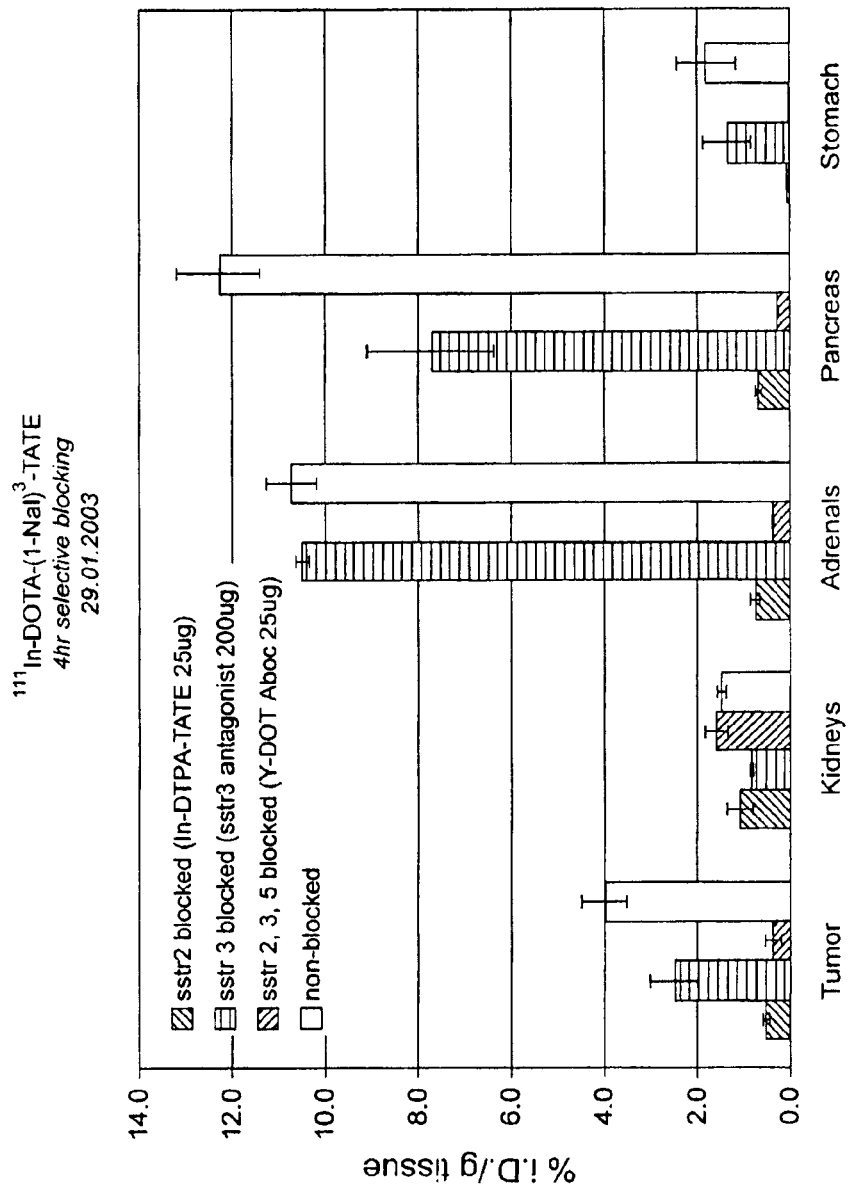
FIG. 1 illustrates a graphical representation of a rat study showing that tumor and non- tumor tissue uptake is receptor specific (except for kidneys) and specifically discloses observed uptake of $^{111}$In-DOTA-[1-Na$^3$]-TATE peptide in somatostatin receptor expressing tissues being blocked by coinjection of non-radioactive, competitor, somatostatin analogs that have various receptor subtype specificity.

The invention will now be described in greater detail with reference to the following specific Examples.

EXAMPLE I

Synthesis of Peptide Compounds

The new peptide compounds or peptide conjugates of the invention are synthesized by Fmoc-solid-phase synthesis on 2-chloro-tritylchloride resin (Int. J. Pept. Protein Res. 35, 1990, 161–214). According to this method Fmoc-protected amino acids are successively coupled, each time followed by cleavage of the protecting Fmoc-group in basic medium. Finally cleavage of the fully protected conjugates from the resin, oxidative cyclization to the cystine-containing cyclic peptide, and introduction of the DOTA-chelator, (e.g. as described by Heppeler et al. in Chem Eur. J. 1999; 5: 1974–1981), leads to the desired peptide compounds comprising the somatostatin analogues (1), (2) and (3), mentioned hereinbefore, as the somatostatin analogues carrying DOTA as the metal-chelating moiety, linked to the N-terminal free amino group of the peptide.

EXAMPLE II

Labeling of Peptide Compounds

The above DOTA carrying peptide compounds (1) and (3) are labeled with $^{111}$In by dissolving each compound in 0.01 M acetic acid, mixing this solution with $^{111}$InCl$_3$— solution (1 mCi/100 µl) in 0.05 M aqueous sodium acetate at higher temperature, and finally neutralizing the solution with HEPES buffer. Labeling with $^{90}$Y, obtained from a $^{90}$Sr—$^{90}$Y radionuclide generator, is performed as follows. A solution of each of the above DOTA carrying peptide compounds (1) and (3) in 0.01 M acetic acid is treated with $^{90}$Y (1.0 mCi/50 µl 0.5 M acetate solution). The mixture is left for approx. 1 hr at higher temperature to effect chelation.

EXAMPLE III

In Vitro Binding Experiments

In vitro binding affinities are determined using transfected cell lines with somatostatin human receptor subtypes (hsst) 2, 3 and 5, as described by Reubi et al. in Eur. J. Nucl. Med. 27, 2000, 273–282. The affinity profiles (IC$_{50}$ values), determined for these somatostatin receptor subtypes, are presented in Tables I and II below. In these tables the results of labeled peptide compounds according to the invention, viz. $^{90}$Y-labelled DOTA-(D)Phe-cyclo[Cys-(D)1-Nal-(D)Trp-Lys-Thr-Cys]-Thr-ol (Y-DOTA-[1-Nal$^3$]-OC; cpd. 8) and $^{90}$Y-labelled DOTA-(D)Phe-cyclo[Cys-(D)3-benzothienyla-lanyl-(D)-Trp-Lys-Thr-Cys]-Thr-ol (Y-DOTA-[BzThi$^3$]-OC; cpd. 9), are compared with those of Y-DOTA-[2-Nal$^3$]-OC (cpd. 10) and Y-DOTA-[3-Pya$^3$]-OC (cpd. 11), referenced to the respective data of somatostatin 28 (cpd. 0) (Table II). Compounds 10 and 11 are prepared according to a method corresponding to the synthesis of compounds 8 and 9: see Examples I and II. For purpose of comparison, recently published results (Reubi et al.—see above) of an additional series of IC$_{50}$ values are also presented in Table I: OC to Y-DOTA-TOC (cpds. 4–7), also referred to the corresponding data of somatostatin S28 (SS-28; cpd. 0).

TABLE I

| Cpd. No. | Compound | hsst 2 | hsst 3 | hsst 5 |
| --- | --- | --- | --- | --- |
| 0 | SS-28 | 2.7 ± 0.3 (19) | 7.7 ± 0.9 (15) | 4.0 ± 0.3 (19) |
| 4 | OC | 2.0 ± 0.7 (5) | 187 ± 55 (3) | 22 ± 6 (5) |
| 5 | Y-DOTA-OC | 20 ± 2 (5) | 27 ± 8 (5) | 57 ± 22 (4) |
| 6 | Y-DOTA-LAN | 23 ± 5 (4) | 290 ± 105 (4) | 16 ± 3.4 (4) |
| 7 | Y-DOTA-TOC | 11 ± 1.7 (6) | 389 ± 135 (5) | 114 ± 29 (5) |

Affinity profiles (IC$_{50}$) for human sst (hsst) 2, 3 and 5 receptors.

All values are IC$_{50}$ ± SEM in nM. The number of experiments is given in parentheses.

OC = Octreotide = H-(D)Phe$^1$-cyclo[Cys$^2$-Phe$^3$-(D)Trp$^4$-Lys$^5$-Thr$^6$-Cys$^7$]-Thr$^8$-ol LAN = Lanreotide = H-(D)2-Nal-cyclo[Cys-Phe-(D)Trp-Lys-Val-Cys]-Thr-NH$_2$ TOC = H-(D)Phe-cyclo[Cys-Tyr-(D)Trp-Lys-Thr-Cys]-Thr-ol

TABLE II

| Cpd. No. | Compound | hsst 2 | hsst 3 | hsst 5 |
| --- | --- | --- | --- | --- |
| 0 | SS-28 | 2.7 ± 0.3 (8) | 3.7 ± 0.3 (8) | 2.9 ± 0.4 (8) |
| 8 | Y-DOTA-[1-Nal$^3$]-OC | 3.3 ± 0.2 (3) | 26 ± 1.9 (3) | 10 ± 1.6 (3) |
| 9 | Y-DOTA-[BzThi$^3$]-OC | 3.4 | 13 | 4.1 |
| 10 | Y-DOTA-[2-Nal$^3$]-OC | 25 ± 1.0 (2) | 133 ± 68 (2) | 98 ± 12.5 (2) |
| 11 | Y-DOTA-[3-Pya$^3$]-OC | 22 ± 9 (4) | 205 ± 43 (4) | 648 ± 165 (4) |

The above results show that the peptide compounds according to the present invention (cpds. 8 and 9) have a highly promising affinity profile with respect to somatostatin receptors. They are binding in the same range or even better to sst 5 as cpd. 6 and have significantly higher affinity than cpd. 5 for this receptor, even taken into account the different values for the SS-28 (cpd. 0) determined in separate laboratories (Table I and II). The affinity of cpd. 8 to sst 3 is in the same order of magnitude as for cpd. 5, but approx. five times better than for cpd. 6; compound 9 is even significantly better. Most surprising, however, is the affinity to the important receptor sst 2. Both compounds 8 and 9 have an approx. three times better binding affinity to sst 2 than even compound 7. From the above tables it will be clear, that compounds 10 and 11 have only moderate to low binding affinities to sst 2, 3 and 5.

EXAMPLE IV

Internalization Experiments

The above favorable binding affinity has been confirmed in internalization experiments. Four $^{111}$In-labelled compounds, viz. $^{111}$In-labelled DOTA-[2-Nal$^3$]-OC, $^{111}$In-labelled DOTA-TOC, $^{111}$In-labelled DOTA-OC and an $^{111}$In-labelled peptide compound of the invention, viz. $^{111}$In-labelled DOTA-[1-Nal$^3$]-OC (DOTA-NOC), were tested in parallel in the same internalization assay. The experiments were carried out using 2.5 pmol $^{111}$In-labelled peptide compound per 1 million AR42J cells. The internalization rate is clearly highest with the labeled peptide compound of the present invention, viz. $^{111}$In-labelled DOTA-NOC: at 4 hours 26.6% injected dose (ID) per 1 million cells, compared with 12.0% ID/mio-cells for labeled DOTA-TOC, 8.0% ID/mio-cells for labeled DOTA-OC and only 0.6% ID/mio-cells for labeled DOTA-[2-Nal$^3$]-OC.

EXAMPLE V

Biodistributions In Vivo

Biodistributions were carried out in tumor bearing Lewis rats. $^{111}$In-labelled DOTA-NOC was used for these experiments and injected in Lewis rats bearing CA 20948 or AR42J tumors (see M. de Jong et al.: Eur. J. Nucl Med. 24, 1997, 368–371). In these biodistribution studies $^{111}$In-labelled DOTA-NOC according to the present invention showed a significant higher tumor uptake and lower kidney uptake than $^{111}$In-labelled DOTA-TOC, in comparison tests.

EXAMPLE VI

Binding Affinity

The following example provides comparative data regarding peptides of the formula: (D)Phe$^1$-cyclo[Cys$^2$-A$^3$-(D)Trp$^4$-Lys$^5$-Thr$^6$-Cys$^7$]-A$^8$ wherein the amino acid at position A$^8$ is L-threonine and the amino acid at position A$^3$ is selected from the group consisting of 3-Iodo-Tyrosine (hereinafter 3-I-Tyr), 3-Benzothienlyalanine (hereinafter 3-BzThi) and 1-Napthylalanine (hereinafter 1-Nal). The latter three have the following structures:

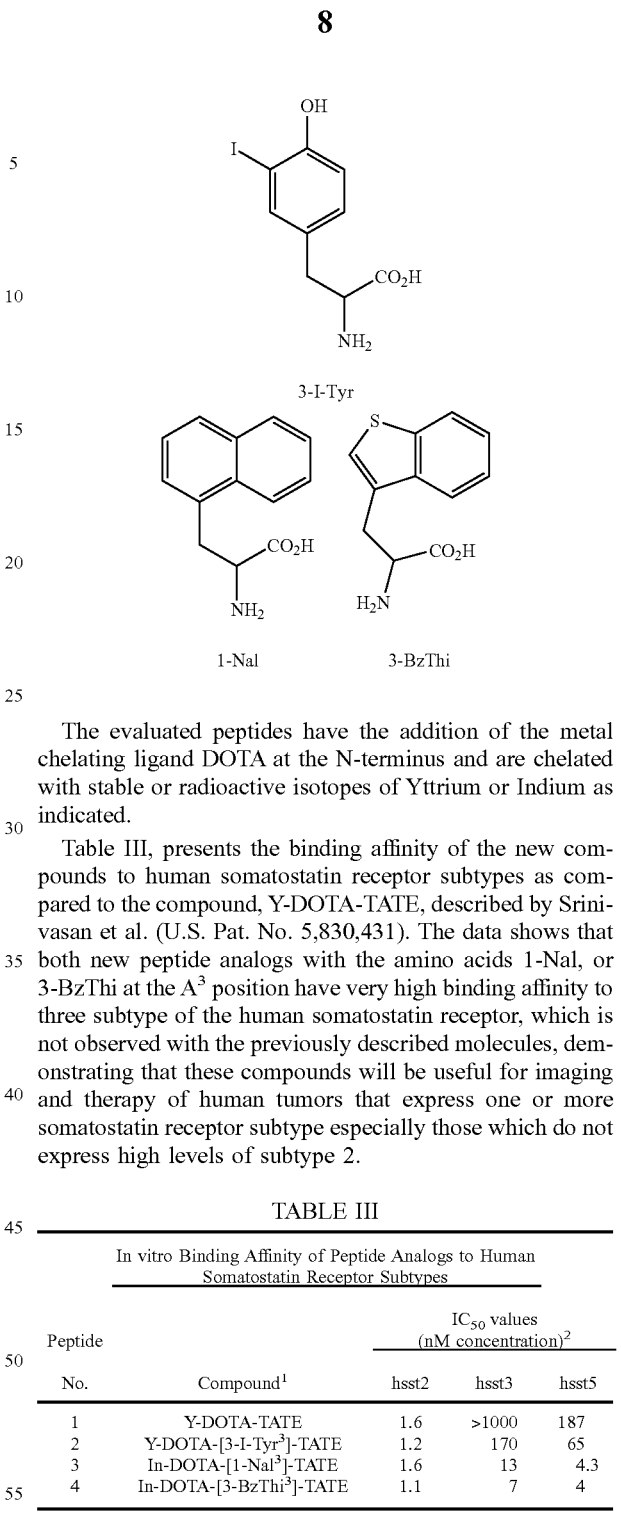

The evaluated peptides have the addition of the metal chelating ligand DOTA at the N-terminus and are chelated with stable or radioactive isotopes of Yttrium or Indium as indicated.

Table III, presents the binding affinity of the new compounds to human somatostatin receptor subtypes as compared to the compound, Y-DOTA-TATE, described by Srinivasan et al. (U.S. Pat. No. 5,830,431). The data shows that both new peptide analogs with the amino acids 1-Nal, or 3-BzThi at the A$^3$ position have very high binding affinity to three subtype of the human somatostatin receptor, which is not observed with the previously described molecules, demonstrating that these compounds will be useful for imaging and therapy of human tumors that express one or more somatostatin receptor subtype especially those which do not express high levels of subtype 2.

TABLE III

In vitro Binding Affinity of Peptide Analogs to Human Somatostatin Receptor Subtypes

| Peptide No. | Compound$^1$ | IC$_{50}$ values (nM concentration)$^2$ | | |
|---|---|---|---|---|
| | | hsst2 | hsst3 | hsst5 |
| 1 | Y-DOTA-TATE | 1.6 | >1000 | 187 |
| 2 | Y-DOTA-[3-I-Tyr$^3$]-TATE | 1.2 | 170 | 65 |
| 3 | In-DOTA-[1-Nal$^3$]-TATE | 1.6 | 13 | 4.3 |
| 4 | In-DOTA-[3-BzThi$^3$]-TATE | 1.1 | 7 | 4 |

Derivatives of the claimed sequence:

(D)Phe$^1$-cyclo[Cys$^2$-A$^3$-Trp$^4$-Lys$^5$-Thr$^6$-Cys$^7$]-Thr$^8$

Where peptide No. 1 is the comparison peptide with the natural amino acid, L-Tyrosine, at the A$^3$ position and peptides No. 2 through 4 are compounds of the invention. Peptides are DOTA-ligand linked at the N-terminal position and the DOTA ligand is complexed with stable isotopes of Y (Yttrium-89) or In (Indium-114), and A$^3$ is one of the amino acids listed in FIG. 1, and the C-terminal amino acid (A$^8$) is Threonine. IC$_{50}$ values were determined as described by Reubi et al. (Eur J Nuc Med 28:836–846, 2001).

EXAMPLE VII

Biodistribution Data

Table IV and Table V present the biodistribution properties of Indium-111 radiolabeled versions of the new compounds in a rat tumor model, and show that the compounds have excellent biodistribution characteristics. Most notable are rapid blood clearance, high tumor uptake, predominately renal excretion, and low uptake in tissues which do not express somatostatin receptors. Somostatin receptors are present at high levels in tumor, pancreas and adrenals.

TABLE IV

Biodistribution of $^{111}$In-DOTA-(1-Nal)$^3$-TATE in AR42J Tumor Bearing Lewis Rats (Percent Injected Dose per Gram Tissue).

| Tissue | 4 hr ± StdDev | 24 hr ± StdDev | 48 h ± StdDev |
| --- | --- | --- | --- |
| Blood | 0.04 ± 0.00 | 0.00 ± 0.00 | 0.00 ± 0.00 |
| Tumor | 4.01 ± 0.50 | 1.82 ± 0.26 | 1.11 ± 0.05 |
| Kidneys | 1.51 ± 0.09 | 0.75 ± 0.12 | 0.74 ± 0.08 |
| Adrenals | 10.76 ± 0.55 | 5.87 ± 1.40 | 5.22 ± 0.30 |
| Pancreas | 12.31 ± 0.88 | 2.45 ± 0.31 | 2.16 ± 0.24 |
| Spleen | 0.11 ± 0.01 | 0.04 ± 0.00 | 0.04 ± 0.01 |
| Stomach | 1.83 ± 0.62 | 0.92 ± 0.11 | 0.42 ± 0.33 |
| Bowel | 0.25 ± 0.07 | 0.17 ± 0.00 | 0.14 ± 0.01 |
| Liver | 0.09 ± 0.06 | 0.04 ± 0.01 | 0.06 ± 0.03 |
| Lung | 0.09 ± 0.01 | 0.03 ± 0.00 | 0.02 ± 0.01 |
| Heart | 0.02 ± 0.00 | 0.01 ± 0.00 | 0.01 ± 0.00 |
| Bone | 0.02 ± 0.00 | 0.01 ± 0.00 | 0.00 ± 0.00 |

TABLE V

Biodistribution of $^{111}$In-DOTA-(BzThi)$^3$-TATE in AR42J Tumor Bearing Lewis Rats (Percent Injected Dose per Gram Tissue).

| Tissue | 4 hr ± StdDev | 24 hr ± StdDev | 48 h ± StdDev |
| --- | --- | --- | --- |
| Blood | 0.02 ± 0.00 | 0.01 ± 0.00 | 0.01 ± 0.01 |
| Tumor | 4.12 ± 0.62 | 2.05 ± 0.75 | 1.10 ± 0.18 |
| Kidneys | 1.79 ± 0.15 | 1.83 ± 0.17 | 0.94 ± 0.30 |
| Adrenals | 5.71 ± 0.53 | 3.34 ± 0.72 | 2.84 ± 0.63 |
| Pancreas | 10.33 ± 0.34 | 3.30 ± 0.20 | 2.53 ± 0.57 |
| Spleen | 0.05 ± 0.01 | 0.05 ± 0.00 | 0.10 ± 0.11 |
| Stomach | 0.81 ± 0.23 | 0.66 ± 0.36 | 0.47 ± 0.07 |
| Bowel | 0.15 ± 0.02 | 0.13 ± 0.01 | 0.18 ± 0.02 |
| Liver | 0.10 ± 0.01 | 0.07 ± 0.01 | 0.10 ± 0.09 |
| Lung | 0.06 ± 0.00 | 0.05 ± 0.00 | 0.10 ± 0.13 |
| Heart | 0.01 ± 0.00 | 0.01 ± 0.00 | 0.01 ± 0.00 |
| Bone | 0.01 ± 0.01 | 0.01 ± 0.00 | 0.01 ± 0.00 |

EXAMPLE VIII

Tissue Uptake

Tumor and non-tumor tissue uptake is receptor specific (except for kidneys) as shown in the rat study presented in FIG. 1, which demonstrates that the observed uptake of $^{111}$In-DOTA-[1-Nal$^3$]-TATE peptide in somatostatin receptor expressing tissues can be blocked by coinjection of non-radioactive, competitor, somatostatin analogs that have various receptor subtype specificity. As expected the efficacy of the unlabeled derivatives to compete with the uptake the radioactive compounds corresponds to expression level of somostatin receptors and specific subtypes.

Having described the invention in detail, those skilled in the art will appreciate that modifications may be made of the invention without departing from its spirit and scope. Therefore, it is not intended that the scope of the invention be limited to the specific embodiments described.

The invention claimed is:

1. A peptide compound of the general formula $$H\text{-}(A^0)_n\text{-}A^1\text{-cyclo}[Cys^2\text{-}A^3\text{-}A^4\text{-}A^5\text{-}A^6\text{-}Cys^7]\text{-}A^8 \quad (I)$$

wherein:
n is 0 or 1,
A is the residue of an amino acid, (L) or (D) if forms exist,
A$^0$ is optionally halogenated Tyr or Phe,
A$^1$ is optionally halogenated Tyr, or optionally halogenated or methylated Phe or Nal,
A$^3$ is 1-Nal or 3-benzothienylalanyl,
A$^4$ is Trp, optionally N-methylated in its side-chain,
A$^5$ is Lys, optionally N-methylated in its side-chain,
A$^6$ is Thr, Val, Ser, Phe or Ile, and
A$^8$ is Thr, Trp or Nal, wherein the terminal carboxy group may be modified to an alcohol or an, optionally C1–C3 alkylated, amide group.

2. A peptide compound of the general formula $$H\text{-}(Á^0)_n\text{-}Á^1\text{-cyclo}[Cys^2\text{-}A^3\text{-}(D)Trp^4\text{-}Lys^5\text{-}Á^6\text{-}Cys^7]\text{-}Á^8 \quad (II)$$

wherein:
n is 0 or 1,
Á is the residue of an amino acid, (L) or (D) if forms exist,
Á$^0$ is optionally halogenated Tyr,
Á$^1$ is optionally halogenated Tyr, or Phe or Nal,
A$^3$ is 1-Nal or 3-benzothienylalanyl,
Á$^6$ is Thr or Val, and
Á$^8$ is Thr-ol, Thr-OH or Thr-NH$_2$.

3. A peptide compound as in claim 1, wherein the peptide compound has a chelating group selected from the group consisting of (i) N$_2$S$_2$-, N$_3$S- and N$_4$-tetradentate ring structure containing groups, (ii) isocyanate, carbonyl, formyl, diazonium, isothiocyanate and alkoxycarbimidoyl containing groups, (iii) groups derived from N-containing di- and polyacetic acids and their derivatives, and (iv) 2-iminothiolane and 2iminothiacyclohexane containing groups.

4. A peptide compound as in claim 1, wherein the peptide compound has a chelating group derived from ethylenediamine tetraacetic acid (EDTA), diethylenetriamine pentaacetic acid (DTPA), ethyleneglycol-OO'-bis(2-aminoethyl)-N,N,N',N'-tetraacetic acid (EGTA), N,N'-bis (hydroxybenzyl)ethylenediamine-N,N'-diacetic acid (HBED), triethylenetetramine hexaacetic acid (TTHA), substituted EDTA or DTPA, 1,4,7,10-tetraazacyclododecane-N,N',N'',N'''-tetraacetic acid (DOTA), 1,4,7-triazacyclonane-1,4,7-triacetic acid (NOTA) or 1,4,8,11-tetraazacyclotetradecane-N,N',N'',N'''-tetraacetic acid (TETA).

5. A kit for preparing a pharmaceutical composition comprising (i) a peptide compound as claimed in claim 1 or 2, (ii) a solution of a radionuclide compound, said radionuclide compound being selected from the group consisting of $^{99m}$Tc, $^{203}$Pb, $^{66}$Ga, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{24}$Na, $^{157}$Gd, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{109}$Pd, $^{165}$Dy, $^{177}$Lu, $^{161}$Tb, $^{211}$At, $^{123m}$Rh and $^{153}$Sm, and (iii) instructions for use with a prescription for reacting the ingredients present in the kit.

6. A peptide compound as in claim 2, in which the peptide compound has a chelating group selected from the group consisting of (i) N$_2$S$_2$-, N$_3$S- and N$_4$-tetradentate ring structure containing groups, (ii) isocyanate, carbonyl, formyl, diazonium, isothiocyanate and alkoxycarbimidoyl containing groups, (iii) groups derived from N-containing di- and polyacetic acids and their derivatives, and (iv) 2-iminothiolane and 2-iminothiacyclohexane containing groups.

7. A peptide compound as in claim 2, in which the peptide compound has a chelating group derived from ethylenediamine tetraacetic acid (EDTA), diethylenetriamine pentaacetic acid (DTPA), ethyleneglycol-OO'-bis(2-aminoethyl)-N,N,N',N'-tetraacetic acid (EGTA), N,N'-bis(hydroxybenzyl)ethylenediamine-N,N'-diacetic acid (HBED), triethylenetetramine hexaacetic acid (TTHA), substituted EDTA or DTPA, 1,4,7,10-tetraazacyclododecane-N,N',N'',N'''-tetraacetic acid (DOTA), 1,4,7-triazacyclonane-1,4,7-triacetic acid (NOTA) or 1,4,8,11-tetraazacyclotetradecane-N,N',N'',N'''-tetraacetic acid (TETA).

8. A peptide compound as claimed in one of claims 1–4, 6, or 7, wherein the compound is labeled with an element selected from the group consisting of gamma- or positron-emitting radionuclides, Auger-electron-emitting isotopes, paramagnetic ions of nonradioactive elements, and a therapeutic radionuclide.

9. A pharmaceutical composition comprising a peptide compound as in claim 8 and a pharmaceutically acceptable carrier.

10. A composition as claimed in claim 9, wherein the peptide compound is labeled with a gamma- or positron-emitting radionuclide, or with a paramagnetic ion of a nonradioactive element.

11. A method for detecting and localizing tissues having somatostatin receptors in the body of a warm-blooded living being, which comprises (i) administering to said being a composition as claimed in claim 10, comprising the active substance in a quantity sufficient for external imaging, and thereupon (ii) subjecting said being to external imaging to determine the targeted sites in the body of said being in relation to the background activity, in order to allow detection and localization of said tissues in said body.

12. A composition as claimed in claim 9, wherein the peptide compound is labeled with a therapeutic radionuclide.

13. A method for the therapeutic treatment of tumors having on their surface somatostatin receptors in the body of a warm-blooded living being, which comprises administering to said being a composition as claimed in claim 12, comprising the active substance in a quantity effective for combating or controlling tumors.

14. A pharmaceutical composition comprising:
a. a peptide compound as in claim 8;
b. a pharmaceutically acceptable carrier; and
c. at least one pharmaceutically acceptable adjuvant.

15. A composition as claimed in claim 14, wherein the peptide compound is labeled with a gamma- or positron-emitting radionuclide, or with a paramagnetic ion of a nonradioactive element.

16. A composition as claimed in claim 14, wherein the peptide compound is labeled with a therapeutic radionuclide.

17. A peptide compound as in one of claims 1–4, 6, or 7, wherein the compound is labeled with a gamma- or positron-emitting radionuclide, selected from the group consisting of $^{99m}Tc$, $^{203}Pb$, $^{66}Ga$, $^{67}Ga$, $^{68}Ga$, $^{72}As$, $^{111}In$, $^{113m}In$, $^{97}Ru$, $^{62}Cu$, $^{64}Cu$, $^{52}Fe$, $^{51}Cr$, $^{24}Na$, $^{157}Gd$, $^{52m}Mn$, 162Dy, $^{123}I$, $^{131}I$, $^{75}Br$ and $^{76}Br$, or with a paramagnetic ion of an element, selected from the group consisting of nonradioactive Gd, Fe, Mn and Cr.

18. A peptide compound as in one of claims 1–4, 6, or 7 wherein the compound is labeled with a therapeutic radionuclide, selected from the group consisting of $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Au$, $^{109}Pd$, $^{165}Dy$, $^{177}Lu$, $^{161}Tb$, $^{123m}Rh$, $^{211}At$, $^{111}In$ and $^{153}Sm$.

19. A kit for preparing a pharmaceutical composition comprising (i) a peptide compound as claimed in claim 1 or 2, (ii) a pharmaceutically acceptable carrier, (iii) a solution of a radionuclide compound, said radionuclide compound being selected from the group consisting of $^{99m}Tc$, $^{203}Pb$, $^{66}Ga$, $^{67}Ga$, $^{68}Ga$, $^{72}As$, $^{111}In$, $^{113m}In$, $^{97}Ru$, $^{62}Cu$, $^{64}Cu$, $^{52}Fe$, $^{52m}Mn$, $^{51}Cr$, $^{24}Na$, $^{157}Gd$, $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Au$, $^{109}Pd$, $^{165}Dy$, $^{177}Lu$, $^{161}Tb$, $^{211}At$, $^{123m}Rh$ and $^{153}Sm$, and (iv) instructions for use with a prescription for reacting the ingredients present in the kit.

20. A kit for preparing a pharmaceutical composition comprising (i) a peptide compound as claimed in claim 1 or 2, (ii) a pharmaceutically acceptable carrier, (iii) a pharmaceutically acceptable adjuvant, (iv) a solution of a radionuclide compound, said radionuclide compound being selected from the group consisting of $^{99m}Tc$, $^{203}Pb$, $^{66}Ga$, $^{67}Ga$, $^{68}Ga$, $^{72}As$, $^{111}In$, $^{113m}In$, $^{97}Ru$, $^{62}Cu$, $^{64}Cu$, $^{52}Fe$, $^{52m}Mn$, $^{51}Cr$, $^{24}Na$, $^{157}Gd$, $^{186}Re$, 188Re, $^{77}As$, $^{90}Y$, $^{67}Cu$, $^{169}Er$, $^{121}Sn$, $^{127}Te$, $^{142}Pr$, $^{143}Pr$, $^{198}Au$, $^{109}Pd$, $^{165}Dy$, $^{177}Lu$, $^{161}Tb$, $^{211}At$, $^{123m}Rh$ and $^{153}Sm$, and (v) instructions for use with a prescription for reacting the ingredients present in the kit.

* * * * *